United States Patent
Sirichandra

(10) Patent No.: US 10,966,913 B2
(45) Date of Patent: Apr. 6, 2021

(54) COSMETIC USE OF SPICULISPORIC ACID AS A DEODORANT ACTIVE AGENT

(71) Applicant: L'OREAL, Paris (FR)

(72) Inventor: Caroline Sirichandra, Joinville le Pont (FR)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 15/324,886

(22) PCT Filed: Jul. 10, 2015

(86) PCT No.: PCT/FR2015/051917
§ 371 (c)(1),
(2) Date: Jan. 9, 2017

(87) PCT Pub. No.: WO2016/005707
PCT Pub. Date: Jan. 14, 2016

(65) Prior Publication Data
US 2017/0209357 A1 Jul. 27, 2017

(30) Foreign Application Priority Data
Jul. 10, 2014 (FR) ..................... 14 56648

(51) Int. Cl.
*A61K 8/49* (2006.01)
*A61K 8/44* (2006.01)
*A61K 8/41* (2006.01)
*A61Q 15/00* (2006.01)
*A61K 8/362* (2006.01)

(52) U.S. Cl.
CPC ............ *A61K 8/4973* (2013.01); *A61K 8/362* (2013.01); *A61K 8/41* (2013.01); *A61K 8/44* (2013.01); *A61Q 15/00* (2013.01); *A61K 2800/31* (2013.01); *A61K 2800/874* (2013.01)

(58) Field of Classification Search
None
See application file for complete search history.

(56) References Cited

U.S. PATENT DOCUMENTS

| 6,716,436 B1 * | 4/2004 | Seguin | A61K 8/44 424/401 |
| 2012/0070396 A1 * | 3/2012 | Suzuki | A61K 8/60 424/64 |

FOREIGN PATENT DOCUMENTS

| EP | 2 055 314 A1 | 5/2009 |
| JP | 2002047137 A * | 2/2002 |
| KR | 20060111183 A | 10/2006 |
| WO | WO-9843604 A1 * | 10/1998 | ............. A61K 8/347 |

OTHER PUBLICATIONS

Kaise et al., EPO translation of JP, 2002047137 accessed May 9, 2017.*
Ishigami (Ishigami, Y., et al., Surface Active Properties of Biosoap from Spiculisporic Acid, Journal of Colloid and Interface Science, 94 (1983), pp. 131-139). (Year: 1983).*
Rahman et al., "Production, Characterisation and Applications of Biosurfactants—Review", Biotechnology, 7(2): 360-370, 2008.
English abstract for KR-20060111183-A.
Ishigami et al., "Surface Active Properties of Biosoap from Spiculisporic Acid", Journal of Colloid and Interface Science, 94(1): 131-139, Jul. 1983.

* cited by examiner

*Primary Examiner* — Dominic Lazaro
(74) *Attorney, Agent, or Firm* — Polsinelli PC

(57) ABSTRACT

The invention relates to the cosmetic use, as a deodorant active agent, of spiculisporic acid in free form, partially or fully neutralised by at least one mineral and/or organic base. The invention also relates to a cosmetic method for treating human body odours, in particular the armpits or feet, in which at least one spiculisporic acid as defined above or a composition containing same in a physiologically acceptable medium is applied to the human keratin material.

19 Claims, No Drawings

COSMETIC USE OF SPICULISPORIC ACID AS A DEODORANT ACTIVE AGENT

CROSS REFERENCE TO RELATED APPLICATIONS

This application is a National Phase filing under 35 U.S.C. § 371 of PCT/FR2015/051917 filed on Jul. 10, 2015; and this application claims priority to Application No. 1456648 filed in France on Jul. 10, 2014 under 35 U.S.C. § 119. The entire contents of each application are hereby incorporated by reference.

The present invention relates to the cosmetic use, as a deodorant active agent, of spiculisporic acid and/or salts thereof.

The present invention relates to the cosmetic use, as a deodorant active agent, of spiculisporic acid, spiculisporic acid being in free form or in a form partially neutralized or totally neutralized with at least one mineral base and/or one organic base, and more particularly in a composition comprising a physiologically acceptable medium.

The invention also relates to a cosmetic process for treating human body odors, in particular of the armpits or feet, which consists in applying to the human keratin materials at least one spiculisporic acid as defined previously or a composition containing same in a physiologically acceptable medium.

Spiculisporic acid, also known by the name 4,5-dicarboxy-4-pentadecanolide, has the following formula:

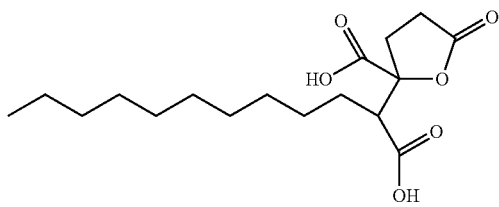 [SMILES: CCCCCCCCCCC(C(=O)O)C1(C(=O)O)CCC(=O)O1]

It is known from the prior art that at room temperature, spiculisporic acid (S-acid) is insoluble in water and fatty substances, but is soluble in ethanol. At room temperature, spiculisporic acid may be dissolved in water by salification. The possibility of forming three salts has been demonstrated; the sodium salts have been characterized:

- S-1Na, the monosodium salt, corresponding to the product of neutralization of the carboxylic group bonded to the carbon atom in position C4 of S-acid;
- S-2Na, the disodium salt, corresponding to the product of neutralization of the carboxylic groups bonded to the carbon atoms in positions C4 and C5 of S-acid;
- S-3Na, the trisodium salt, corresponding to the product of saponification of the lactone function of S-2Na.

It is especially known that spiculisporic acid has surfactant properties.

Furthermore, it is known that the unpleasant odors of perspiration are related in particular to the presence of microorganisms and more particularly *Corynebacterium xerosis*. In point of fact, sweat is in itself relatively odorless when it is secreted. It is the degradation by bacteria via enzymatic reactions which produces malodorous compounds. Deodorant active agents have the function, precisely, of reducing or preventing the formation of unpleasant odors.

The various systems proposed hitherto may be grouped into major families. Among them there are antibacterial substances that destroy the resident bacterial flora. The product most commonly used is Triclosan. There are also substances that reduce bacterial growth. Among these substances, mention may be made of transition-metal-chelating agents such as ethylenediaminetetraacetic acid (EDTA) or diethylenetriaminepentaacetic acid (DTPA).

However, these various treatments, applied to the skin of the armpits, have a tendency to bring about detrimental changes in the skin.

There is thus still a need to find novel deodorant active agents which are effective. In one particular mode, there is also still a need to find novel deodorant active agents which are effective and which do not have these drawbacks.

The inventors have revealed antibacterial activity toward microorganisms responsible for unpleasant body odors, especially *Corynebacterium xerosis*, of spiculisporic acid, especially of spiculisporic acid neutralized with an organic base, in particular with L-arginine in a 1/1 mole ratio, such that it may be of use in a composition, preferably a deodorant and/or antiperspirant cosmetic composition.

The present invention relates to the cosmetic use, as a deodorant active agent, of spiculisporic acid in free form or in a form partially neutralized or totally neutralized with at least one mineral base and/or one organic base, in particular spiculisporic acid partially or totally neutralized with at least one organic base, and more particularly in a composition comprising a physiologically acceptable medium.

The invention also relates to a cosmetic process for treating human body odors, in particular of the armpits or feet, which consists in applying to the human keratin materials at least one spiculisporic acid as defined previously or a composition containing same in a physiologically acceptable medium.

The present invention also relates to a composition comprising, in a physiologically acceptable medium:
  a) at least one spiculisporic acid in free form or in a form partially neutralized or totally neutralized with at least one mineral base and/or one organic base, and
  b) at least one additional deodorant active agent and/or at least one antiperspirant active agent.

It also relates in particular to a composition packaged
  (i) in pressurized form in an aerosol device or in a pump-action bottle;
  (ii) in a device equipped with an openwork wall, especially a grate;
  (iii) in a device equipped with a ball applicator ("roll-on");
  (iv) in the form of a wand (stick); or
  (v) in the form of a loose or compacted powder,
characterized in that it contains, in a physiologically acceptable medium, a spiculisporic acid as defined previously.

In the context of the present invention, the term "deodorant active agent" refers to any substance that is capable of masking, absorbing, improving and/or reducing the unpleasant odor resulting from the decomposition of human sweat by bacteria.

The term "antiperspirant active agent" means a salt which, by itself, has the effect of reducing the flow of sweat, of reducing the sensation on the skin of moisture associated with human sweat or of masking human sweat.

Within the meaning of the present invention, the term "physiologically acceptable medium" is intended to denote a medium that is suitable for the topical administration of a composition.

A physiologically acceptable medium generally has no unpleasant odor or appearance, and is entirely compatible with topical administration.

In the present case, where the composition is intended for topical administration, i.e. by application at the surface of the keratin material under consideration, such a medium is considered in particular to be physiologically acceptable when it does not cause stinging, tautness or redness that is unacceptable to the user.

Spiculisporic Acid

Spiculisporic acid, also known by the name 4,5-dicarboxy-4-pentadecanolide, has the following formula:

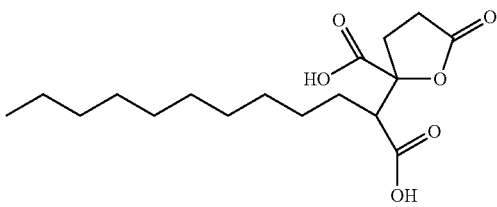 [SMILES: CCCCCCCCCCC(C(=O)O)C1(C(=O)O)CCC(=O)O1]

In the context of the present invention, spiculisporic acid may be in free form or in a form partially neutralized or totally neutralized with at least one mineral base and/or one organic base, and more particularly in a composition comprising a physiologically acceptable medium.

In a particular embodiment according to the invention, spiculisporic acid may be in free form or in a form partially neutralized or totally neutralized with at least one mineral base and/or one organic base in a composition comprising a physiologically acceptable medium, and also comprising at least one surfactant.

In the context of the invention, and unless otherwise mentioned, the ratio R1 corresponds to the ratio of the number of moles of base to the number of moles of spiculisporic acid. It is thus a mole ratio. Mention may be made, for example, of a mole ratio R1 strictly greater than 1.0 and preferably less than or equal to 2.50. Thus, a mole ratio R1 strictly greater than 1.0 corresponds to a number of moles of base strictly greater than the number of moles of spiculisporic acid.

According to one embodiment, the ratio R1 is strictly greater than 1.0. Preferably, the ratio R1 is between 1.0 and 2.50. More particularly, the ratio R1 is greater than or equal to 1.10 and less than or equal to 2.0.

In particular, the ratio R1 is equal to 1.10.

According to one embodiment, the ratio denoted R2, of the mass of spiculisporic acid to the mass of surfactant(s), other than the S-acid, is less than or equal to 12.50.

According to one embodiment, the ratio R2 is between 0.1 and 12.5. In particular, the ratio R2 is between 1.0 and 12.50. Preferably, the ratio R2 is between 1.0 and 5.0.

In the context of the invention, and unless otherwise mentioned, the ratio R2 corresponds to the ratio of the mass of spiculisporic acid to the mass of surfactant(s). It is thus a mass ratio.

By way of example, spiculisporic acid is available under the trade name Spiculisporic Acid® from the company Iwata Chemical.

According to the invention, the spiculisporic acid content may range from 0.1% to 15% by mass relative to the total mass of said composition.

According to a preferred embodiment, the spiculisporic acid content is between 0.1% and 15%, preferably between 0.5% and 10% and preferentially between 1% and 10% by mass of active material relative to the total mass of the composition.

Composition

Surfactants

In a particular embodiment of the invention, spiculisporic acid is included in a composition comprising a physiologically acceptable medium, which also comprises at least one surfactant.

The surfactant(s) according to the invention are chosen from sulfate and/or sulfonate surfactants, and non-sulfate and non-sulfonate surfactants.

In a particular embodiment, spiculisporic acid is included in a composition comprising a physiologically acceptable medium, which also comprises at least one organic base and at least one sulfate and/or sulfonate surfactant.

According to one embodiment, the sulfate and/or sulfonate surfactant is chosen from the group formed from anionic sulfate and/or sulfonate surfactants.

According to one embodiment, the sulfate and/or sulfonate surfactant is an anionic sulfate surfactant, an anionic sulfonate surfactant or a mixture of these surfactants.

In the context of the invention, and unless otherwise mentioned, the term "anionic sulfate surfactant" denotes a surfactant comprising a sulfate group, i.e. an anionic surfactant comprising an —OSO$_3^-$ or —OSO$_3$H group.

According to the invention, the term "anionic sulfonate surfactant" denotes a surfactant comprising a sulfonate group, i.e. an anionic surfactant comprising an —SO$_3^-$ or —SO$_3$H group.

According to one embodiment, the anionic sulfate or sulfonate surfactants according to the invention are chosen from the group formed from alkyl sulfates, alkyl ether sulfates, alkylamido ether sulfates, alkylaryl polyether sulfates, monoglyceride sulfates, sulfonates, isethionates, taurates, sulfosuccinates and alkyl sulfoacetates, and also corresponding salified forms, and mixtures thereof.

These compounds may be oxyethylenated and then preferably comprise from 1 to 50 ethylene oxide units and better still from 1 to 10 ethylene oxide units.

When the anionic surfactant is in salt form, said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Among the anionic sulfonate surfactants, mention may be made in particular of alkylsulfonates, alkylamidesulfonates, alkylarylsulfonates, alpha-olefin-sulfonates and paraffinsulfonates, and mixtures thereof.

Among the isethionates, mention may be made in particular of acylisethionates.

Among the taurates, mention may be made in particular of N-acyltaurates, N-methyltaurates and the corresponding acid forms.

For all the above mentioned compounds, the alkyl and acyl groups preferably comprise from 6 to 30 carbon atoms, better still from 12 to 24 or even from 16 to 22 carbon atoms, and the aryl groups are preferably a phenyl or benzyl group.

According to one embodiment, the sulfate and/or sulfonate surfactant according to the invention is chosen from the group formed from alkyl sulfates, alkyl ether sulfates, sulfonates, isethionates, taurates, sulfosuccinates and alkyl sulfoacetates, and mixtures thereof.

According to the invention, the anionic sulfate or sulfonate surfactants may also be chosen from alkylsulfosuccinates, alkyl ether sulfosuccinates and alkylamide sulfosuccinates, and the corresponding acid forms, the alkyl groups of these compounds comprising from 6 to 30 carbon atoms, better still from 12 to 24 or even from 16 to 22 carbon atoms.

As examples of anionic sulfate and/or sulfonate surfactants, mention may be made more particularly of sodium lauryl sulfate, sodium laureth sulfate, sodium lauryl methyl isethionate, triethanolamine lauryl sulfate, ammonium lauryl sulfate and sodium cetostearyl sulfate, and mixtures thereof.

Examples of sulfonates that may be mentioned include alpha-olefin sulfonates, for instance the sodium alpha-olefin sulfonate (C14-16), sold under the name Bio-Terge AS-40® by the company Stepan, sold under the names Witconate AOS Protégé® and Sulframine AOS PH 12® by the company Witco or sold under the name Bio-Terge AS-40 CG® by the company Stepan, the secondary sodium olefin sulfonate sold under the name Hostapur SAS 30® by the company Clariant; linear alkylarylsulfonates such as the sodium xylenesulfonate sold under the names Manrosol SXS30®, Manrosol SXS40® and Manrosol SXS93® by the company Manro.

Alkyl sulfoacetates that may be mentioned include lauryl sulfoacetate, for instance the product sold as a mixture with sodium methyl-2-sulfolaurate and disodium 2-sulfolaurate under the reference Stepan Mild PCL by the company Stepan. Mention may also be made of the sodium salt of lauryl sulfoacetate under the INCI name Sodium lauryl sulfoacetate and sold under the name Lathanol LAL® by the company Stepan.

Isethionates that may be mentioned include acylisethionates, such as sodium cocoylisethionate, such as the product sold under the name Jordapon CI P® by the company Jordan, and also sodium lauroyl methyl isethionate (for example Iselux LQ-CLR-SB from Innospec).

Taurates that may be mentioned include the sodium salt of palm kernel oil methyltaurate sold under the name Hostapon CT Pate® by the company Clariant; N-acyl N-methyltaurates, for instance the sodium N-cocoyl N-methyltaurate sold under the name Hostapon LT-SF® by the company Clariant or sold under the name Nikkol CMT-30-T® by the company Nikkol, and the sodium palmitoyl methyltaurate sold under the name Nikkol PMT® by the company Nikkol.

Examples of sulfosuccinates that may be mentioned include oxyethylenated (3 EO) lauryl (70/30 C12/C14) alcohol monosulfosuccinate sold under the names Setacin 103 Special® and Rewopol SB-FA 30 K 4® by the company Witco, the disodium salt of a hemisulfosuccinate of C12-C14 alcohols, sold under the name Setacin F Special Paste® by the company Zschimmer Schwarz, the oxyethylenated (2 EO) disodium oleamidosulfosuccinate sold under the name Standapol SH 135® by the company Cognis, the oxyethylenated (5 EO) lauramide monosulfosuccinate sold under the name Lebon A-5000® by the company Sanyo, the disodium salt of oxyethylenated (10 EO) lauryl citrate monosulfosuccinate sold under the name Rewopol SB CS 50® by the company Witco, the disodium salt of lauryl alcohol monosulfosuccinate sold under the name Rewopol SB F12P® by the company Witco, or the ricinoleic monoethanolamide monosulfosuccinate sold under the name Rewoderm S 1333® by the company Witco. Use may also be made of polydimethylsiloxane sulfosuccinates, such as the disodium PEG-12 dimethicone sulfosuccinate sold under the name Mackanate-DC30 by the company Macintyre.

Examples of alkyl ether sulfates that may be mentioned include sodium lauryl ether sulfate (CTFA name: sodium laureth sulfate), such as the product sold under the names Texapon® N40 and Texapon® AOS 225 UP by the company Cognis, or ammonium lauryl ether sulfate (CTFA name: ammonium laureth sulfate), such as the product sold under the name Standapol® EA-2 by the company Cognis, or the ammonium (C12-C14)alkyl ether (9 EO) sulfate sold under the name Rhodapex AB/20® by the company Rhodia Chimie.

Examples of alkyl sulfates that may be mentioned include sodium lauryl sulfate (CTFA name: sodium lauryl sulfate), such as the product sold by the company Tensachem under the name Tensopol USP94, triethanolamine lauryl sulfate (CTFA name: TEA lauryl sulfate), such as the product sold by the company Huntsman under the name Empicol® TL40 FL or the product sold by the company Cognis under the name Texapon® T42, which products are at 40% in aqueous solution. Mention may also be made of ammonium lauryl sulfate (CTFA name: Ammonium lauryl sulfate), such as the product sold by the company Huntsman under the name Empicol® AL 30FL, which is at 30% in aqueous solution.

According to one embodiment, the sulfate and/or sulfonate surfactant is chosen from the group formed from alkyl sulfates, alkyl ether sulfates and isethionates, and mixtures thereof.

In particular, the sulfate and/or sulfonate surfactant is chosen from the group formed from ($C_6$-$C_{24}$)alkyl sulfates, ($C_6$-$C_{24}$)alkyl ether sulfates comprising from 1 to 20, preferably from 2 to 10, ethylene oxide units, isethionates, and mixtures thereof, especially in the form of alkali metal, ammonium, amino alcohol or alkaline-earth metal salts, or a mixture of these compounds.

In particular, use is preferably made of ($C_{12-20}$)alkyl sulfates, ($C_{12-20}$)alkyl ether sulfates comprising from 1 to 20, preferably from 2 to 10, ethylene oxide units, isethionates, especially in the form of alkali metal, ammonium, amino alcohol and alkaline-earth metal salts, or a mixture of these compounds.

According to one embodiment, the sulfate and/or sulfonate surfactant is chosen from the group formed from sodium lauryl sulfate, sodium lauryl ether sulfate comprising 2 to 10 ethylene oxide units, such as the laureth sulfates sold under the names Texapon AOS 225 UP from Cognis or Ifrapon LOS 70 RO 16 from Ecogreen Oleochemicals, and sodium lauryl methyl isethionate, and mixtures thereof.

The cosmetic compositions of the invention may comprise a single surfactant as defined above, or a mixture of surfactants as defined above.

According to the invention, the non-sulfate and non-sulfonate surfactant may be a non-sulfate and non-sulfonate surfactant chosen from the group formed from amphoteric surfactants, anionic surfactants, nonionic surfactants and cationic surfactants, and mixtures thereof.

This surfactant is not an anionic surfactant comprising a sulfate or sulfonate group.

In the context of the invention, and unless otherwise mentioned, the term "anionic surfactant comprising a sulfate group" means an anionic surfactant comprising an —OSO3- or —OSO3H group (sulfate surfactant) and the term "anionic surfactant comprising a sulfonate group" (sulfonate surfactant) means an anionic surfactant comprising an —SO3- or —SO3H group.

In the context of the invention, the "non-sulfate and non-sulfonate surfactant" may be a non-sulfate surfactant (not comprising a sulfate group), a non-sulfonate surfactant (not comprising a sulfonate group) or a non-sulfate and non-sulfonate surfactant (comprising neither a sulfate group nor a sulfonate group).

According to the invention, the surfactant may be an amphoteric surfactant.

The amphoteric surfactants (this term including amphoteric and zwitterionic surfactants) may be chosen, for example, from betaines, N-alkylamido betaines and derivatives thereof, glycine derivatives, sultaines, alkyl polyaminocarboxylates, alkylamphoacetates and lecithins, and mixtures thereof.

Betaines that may especially be mentioned include alkyl betaines, for instance cocoyl betaine, such as the product sold under the name Dehyton AB-30® by the company Cognis, lauryl betaine, such as the product sold under the name Genagen KB® by the company Clariant, oxyethylenated (10 EO) lauryl betaine, such as the product sold under the name Lauryl Ether (10 EO) Betaine® by the company Shin Nihon Rica, or oxyethylenated (10 EO) stearyl betaine, such as the product sold under the name Stearyl Ether (10 EO) Betaine® by the company Shin Nihon Rica.

Among the N-alkylamido betaines and derivatives thereof, examples that may be mentioned include the cocamidopropyl betaine sold under the name Lebon 2000 HG® by the company Sanyo, under the name Empigen BB® by the company Albright & Wilson or under the names Tego Betain F 50 and CK D by the company Evonik Goldschmidt, or those sold as a mixture with glyceryl laurate, such as the commercial references Tego Betain HS or Antil HS 60 from Evonik Goldschmidt, or lauramidopropyl betaine, sold under the name Rewoteric AMB12P® by the company Witco.

Sultaines that may be mentioned include the cocoylamidopropyl hydroxysulfobetaine, sold under the name Crosultaine C-50® by the company Croda.

Alkyl polyaminocarboxylates (APACs) that may be mentioned include sodium cocoylpolyaminocarboxylate, sold under the names Ampholak 7 CX/C® and Ampholak 7 CX® by the company AkzoNobel, sodium stearylpolyamidocarboxylate, sold under the name Ampholak 7 TX/C by the company AkzoNobel, or sodium carboxymethyloleylpolypropylamine, sold under the name Ampholak XO7/C® by the company AkzoNobel.

Examples of alkylamphoacetates that may be mentioned include N-disodium N-cocoyl-N-carboxymethoxyethyl-N-(carboxymethyl)ethylenediamine (CTFA name: disodium cocoamphodiacetate), such as the product sold under the name Miranol C2M Concentrate NP® by the company Rhodia Chimie, N-sodium N-cocoyl-N-hydroxyethyl-N-(carboxymethyl)ethylenediam ine (CTFA name: sodium cocoamphoacetate).

Among the lecithins, mention may be made of phospholipids and lysophospholipids. In particular, mention may be made of the lecithins sold by Nikkol Group (Lecinol Series) or the lecithins sold by Cargil/Lucas Meyer (the Emulmetik and Emulfluid family).

According to one embodiment, the amphoteric surfactant is chosen from the group formed from betaines, N-alkylamido betaines and derivatives thereof, glycine derivatives, sultaines, alkyl polyaminocarboxylates, alkylamphoacetates and lecithins, and mixtures thereof.

According to one embodiment, the amphoteric surfactant is chosen from the group formed from alkyl betaines, alkylamidopropyl betaines and alkylamphoacetates, and mixtures thereof.

According to one embodiment, the surfactant is an amphoteric surfactant chosen from the group formed from cocoyl betaine, cocamidopropyl betaine, disodium cocoamphodiacetate and sodium cocoamphoacetate, and mixtures thereof.

According to one embodiment, the surfactant is cocamidopropyl betaine or disodium cocoamphodiacetate.

According to the invention, the surfactant may be a non-sulfate and non-sulfonate anionic surfactant.

The anionic surfactants may be chosen especially from anionic derivatives of proteins of plant origin, amino acids and amino acid derivatives, phosphates and alkyl phosphates, polypeptides, anionic derivatives of alkyl polyglucoside, soaps (fatty acid salts), soybean oil derivatives, lactic acid derivatives, salts thereof and mixtures thereof, glycyrrhizic acids or lipopeptides (such as the biosurfactant Surfactine lipopeptide of microbial origin).

The anionic derivatives of proteins of plant origin are protein hydrolyzates bearing a hydrophobic group, it being possible for said hydrophobic group to be naturally present in the protein or to be added by reaction of the protein and/or of the protein hydrolyzate with a hydrophobic compound. The proteins are of plant origin and the hydrophobic group may especially be a fatty chain, for example an alkyl chain comprising from 10 to 22 carbon atoms.

As anionic derivatives of proteins of plant origin that may be used in the composition according to the invention, mention may be made more particularly of wheat, soybean, oat or silk protein hydrolyzates comprising an alkyl chain containing from 10 to 22 carbon atoms, and salts thereof. The alkyl chain may especially be a lauryl chain and the salt may be a sodium, potassium and/or ammonium salt. Examples that may be mentioned include the sodium, potassium and/or ammonium salts of hydrolyzates of silk protein modified with lauric acid, such as the product sold under the name Kawa Silk by the company Kawaken; the sodium, potassium and/or ammonium salts of hydrolyzates of wheat protein modified with lauric acid, such as the potassium salt sold under the name Aminofoam W OR by the company Croda (CTFA name: potassium lauroyl wheat amino acids) and the sodium salt sold under the name Proteol LW 30 by the company SEPPIC (CTFA name: sodium lauroyl wheat amino acids); the sodium, potassium and/or ammonium salts of hydrolyzates of oat protein comprising an alkyl chain containing from 10 to 22 carbon atoms and more especially the sodium, potassium and/or ammonium salts of hydrolyzates of oat protein modified with lauric acid, such as the sodium salt sold under the name Proteol OAT (CTFA name: Sodium lauroyl oat amino acids); Proteol SAV 50S (INCI name: sodium cocoyl amino acid), Proteol APL (INCI name: sodium cocoyl apple amino acids) by the company SEPPIC, Amaranth S (INCI name: sodium cocoyl hydrolyzed amaranth proteins), and mixtures thereof.

As phosphates and alkyl phosphates, examples that may be mentioned include monoalkyl phosphates and dialkyl phosphates, such as lauryl monophosphate sold under the name MAP 20® by the company Kao Chemicals, the potassium salt of dodecylphosphoric acid, a mixture of mono- and diester (predominantly diester) sold under the name Crafol AP-31® by the company Cognis, the mixture of octylphosphoric acid monoester and diester, sold under the name Crafol AP-20® by the company Cognis, the mixture of ethoxylated (7 mol of EO) 2-butyloctyl phosphate monoester and diester, sold under the name Isofol 12 7 EO-Phosphate Ester® by the company Condea, the potassium or triethanolamine salt of mono(C12-C13)alkyl phosphate, sold under the references Arlatone MAP 230K-40® and Arlatone MAP 230T-60® by the company Uniqema, or the potassium lauryl phosphate sold under the name Dermalcare MAP XC-99/09® by the company Rhodia Chimie.

The anionic derivatives of alkyl polyglucosides may especially be citrates, tartrates, carbonates and glycerol ethers obtained from alkyl polyglucosides. Examples that may be mentioned include the sodium salt of cocoylpolyglucoside (1,4) tartaric ester, sold under the name Eucarol AGE-ET® by the company Cesalpinia, and the sodium salt of cocoylpolyglucoside (1,4) citric ester sold under the name Eucarol AGE-EC® by the company Cesalpinia.

The soaps may be obtained from a fatty acid that is partially or completely saponified (neutralized) with a basic agent. These are alkali metal or alkaline-earth metal soaps or soaps of organic bases. Use may be made, as fatty acids, of saturated, linear or branched fatty acids comprising from 8 to 30 carbon atoms and preferably comprising from 8 to 22 carbon atoms. This fatty acid may be chosen in particular from palmitic acid, stearic acid, myristic acid and lauric acid, and mixtures thereof.

Examples of basic agents that may be used include alkali metal hydroxides (sodium hydroxide and potassium hydroxide), alkaline-earth metal hydroxides (for example magnesium hydroxide), ammonium hydroxide or else organic bases, such as triethanolamine, N-methylglucamine, lysine and arginine.

The soaps may especially be fatty acid alkali metal salts, the basic agent being an alkali metal hydroxide and preferably potassium hydroxide (KOH).

The amount of basic agent must be sufficient for the fatty acid to be at least partially neutralized.

Mention may especially be made of sodium or potassium laurate, potassium myristate, potassium palmitate, potassium stearate, potassium cocoate or KOH salts of stearic acid formed in situ.

The soybean oil derivatives and salts thereof are in particular the fatty acids and salts of fatty acids derived from soybean oil (the INCI name of which is "glycine soya oil" or "soybean oil") and in particular the salts of alkali metals, such as Na, Li or K, preferably Na or K, and of fatty acids derived from soybean, such as potassium soyate, for instance the product sold by the company Noveon.

Examples of acylamino acids that may be mentioned include the sodium cocoyl glycinate sold by the company Ajinomoto under the name Amilite GCS-12, the sodium cocoyl glycinate sold by the company Ajinomoto under the name Amilite GCK-12, the disodium cocoyl glutamate sold by the company Ajinomoto under the name Amisoft ECS-22SB, the sodium lauroyl glutamate sold by the company Ajinomoto under the name Amisoft LS11, the sodium lauroyl sarcosinate sold by the company SEPPIC under the name Oramix L 30, the sodium and disodium stearoyl glutamates sold by the company Ajinomoto under the names Amisoft HS21 P and HS11 Pf, and the sodium cocoyl sarcosinate sold by the company Zschimmer & Schwarz under the name Protelan LS 9011/C. Mention may also be made of the sodium salt of lauroyl oat amino acids, such as Proteol Oat sold by the company SEPPIC, or the compound whose INCI name is sodium cocoyl amino acids, such as Proteol SAV 5OS from SEPPIC.

The amino acid derivatives may be chosen, for example, from sarcosinates and in particular acylsarcosinates, such as sodium lauroylsarcosinate sold under the name Sarkosyl NL 97® by the company Ciba or sold under the name Oramix L 30® by the company SEPPIC, sodium myristoyl sarcosinate, sold under the name Nikkol Sarcosinate MN® by the company Nikkol, or sodium palmitoyl sarcosinate, sold under the name Nikkol Sarcosinate PN® by the company Nikkol; alaninates, such as sodium N-lauroyl-N-methylamidopropionate, sold under the name Sodium Nikkol Alaninate LN 30® by the company Nikkol or sold under the name Alanone Ale® by the company Kawaken, and triethanolamine N-lauroyl-N-methylalanine, sold under the name Alanone Alta® by the company Kawaken; aspartates, such as the mixture of triethanolamine N-lauroyl aspartate and triethanolamine N-myristoyl aspartate, sold under the name Asparack® by the company Mitsubishi; and citrates.

Mention may also be made of the alkali metal salts of (C10-C22)acylglutamic acids, preferably an alkali metal salt of (C12-C20)acylglutamic acids, for example an alkali metal salt of (C16-C18)acylglutamic acids. The alkali metal salts are, for example, the sodium salts, the potassium salts and the lithium salts, preferably the sodium salts.

Such a salt may especially be an alkali metal salt of stearoylglutamic acid, of lauroylglutamic acid, of a C16 acylglutamic acid, of myristoylglutamic acid, of cocoylglutamic acid or of hydrogenated tallow acylglutamic acid.

Preferably, such a surfactant will be an ionic surfactant chosen from sodium stearoylglutamate, disodium stearoylglutamate, potassium stearoylglutamate, sodium lauroylglutamate, disodium lauroylglutamate, potassium lauroylglutamate, sodium cocoylglutamate and hydrogenated tallow sodium acylglutamate, and mixtures thereof, and preferably sodium stearoyl glutamate.

By way of illustration, an example that may be mentioned is the sodium stearoylglutamate sold by the company Ajinomoto under the reference Amisoft HS 11 PF®.

The lactic acid derivatives or salts thereof may be chosen from acyl lactylic acid derivatives or salts thereof (lactylates), such as stearoyl lactylate, for instance the product sold by the company Oleon NV under the name Radiamuls 2980; sodium stearoyl lactylate, as sold, for example, by the company Oleon NV under the name Radiamuls 2990, by the company Karlshamns AB under the name Akoline SL, by the company Uniqema under the name Priazul 2134 or by Dr Straetmans under the name Dermofeel SL; sodium isostearoyl lactylate, such as the product sold by Uniqema under the name Priazul 2133; sodium behenoyl lactylate, for example sold by the company Rita Corporation under the name Pationic SBL; sodium cocoyl lactylate, such as the product sold by the company Rita under the name Pationic SCL, sodium oleoyl lactylate, sodium lauroyl lactylate (Pationic 138C from Caravan) or sodium caproyl lactylate (Capmul S8L-G from Abitec).

Mention may also be made of the sodium cocoamphoacetate, glycerol, lauryl glucoside, sodium cocoyl glutamate and sodium lauryl glucose carboxylate mixture sold by the company Cognis under the reference Plantapon SF.

In particular, the anionic surfactant is chosen from the group formed from fatty carboxylates, alkyl sarcosinates, alkyl phosphates, alkyl glutamates and acyl glutamates, and mixtures thereof.

According to one embodiment, the surfactant is an anionic surfactant chosen from the group formed from disodium cocoyl glutamate and sodium lauryl sarcosinate, and mixtures thereof.

According to one embodiment, the surfactant is disodium cocoyl glutamate or sodium lauryl sarcosinate.

According to the invention, the surfactant may be a nonionic surfactant.

The nonionic surfactants may be chosen, for example, from alkyl polyglucosides (APG), alkylpolypentosides, alkylpolyxylosides, maltose esters, sucrose esters, hydrophobic gums, polyglycerolated fatty alcohols, oxyalkylenated sugar esters, fatty acid esters of polyethylene glycol, fatty acid esters of sorbitan, glucamine derivatives such as 2-ethylhexyloxycarbonyl N-methylglucamine, and mixtures thereof.

Use is preferably made, as alkyl polyglucosides, of those containing an alkyl group comprising from 6 to 30 carbon atoms and preferably from 8 to 16 carbon atoms and containing a hydrophilic (glucoside) group preferably comprising from 1.2 to 3 saccharide units. Examples that may be mentioned include decyl glucoside (C9/C11 alkyl polyglucoside (1.4)), such as the product sold under the name Mydol 10® by the company Kao Chemicals, the product sold under the name Plantaren 2000 UP® by the company Cognis and the product sold under the name Oramix NS 10® by the company SEPPIC; caprylyl/capryl glucoside, such as the product sold under the name Oramix CG 110® by the company SEPPIC or Plantacare 810 P by the company Cognis; lauryl glucoside, such as the products sold under the names Plantaren 1200 N® and Plantacare 1200® by the company Cognis; cocoyl glucoside, such as the product sold under the name Plantacare 818/UP® by the company Cognis; cetostearyl glucoside, optionally as a mixture with cetostearyl alcohol, sold, for example, under the name Montanov 68 by the company SEPPIC, under the name Tego-Care CG90 by the company Goldschmidt and under the name Emulgade KE3302 by the company Henkel; arachidyl glucoside, for example in the form of the mixture of arachidyl and behenyl alcohols and of arachidyl glucoside sold under the name Montanov 202 by the company SEPPIC; cocoyl ethyl glucoside, for example in the form of the mixture (35/65) with cetyl and stearyl alcohols, sold under the name Montanov 82 by the company SEPPIC, and C12 to C20 alkyl glucosides, such as those sold as a mixture with C14 to C22 fatty alcohols under the reference Montanov L by the company SEPPIC.

The oxyalkylenated sugar esters are especially polyethylene glycol ethers of fatty acid and sugar esters. These oxyalkylenated sugar esters may be chosen, for example, from oxyethylenated glucose esters, such as PEG-120 methyl glucose dioleate, sold under the name Glucamate DOE 120 by the company Amerchol.

The fatty acid esters of polyethylene glycol are preferably C16-C22 fatty acid esters comprising from 8 to 100 ethylene oxide units.

The fatty chain of the esters may be chosen especially from stearyl, behenyl, arachidyl, palmityl and cetyl units, and mixtures thereof, such as cetearyl, and preferably a stearyl chain.

The number of ethylene oxide units may range from 8 to 100, preferably from 10 to 80, better still from 10 to 50. According to a particular embodiment of the invention, this number may range from 20 to 40.

As examples of fatty acid esters of polyethylene glycol, mention may be made of stearic acid esters respectively comprising 20, 30, 40, 50 and 100 ethylene oxide units, such as the products respectively sold under the names Myrj 49 P (polyethylene glycol 20 EO stearate; CTFA name: PEG-20 stearate), Myrj 51, Myrj 52 P (polyethylene glycol 40 EO stearate; CTFA name: PEG-40 stearate), Myrj 53 and Myrj 59 P by the company Croda.

The esters of a C16-C22 fatty acid and of sorbitan are in particular esters of C16-C22 acids and of sorbitan and are formed by esterification with sorbitol of at least one fatty acid comprising at least one saturated or unsaturated linear alkyl chain respectively having from 16 to 22 carbon atoms. These esters may be chosen especially from sorbitan stearates, behenates, arachidonates, palmitates or oleates, and mixtures thereof. Use is preferably made of sorbitan stearates and palmitates, and preferably sorbitan stearates.

As examples of sorbitan esters that may be used in the composition according to the invention, mention may be made of sorbitan monostearate (CTFA name: Sorbitan stearate), sold by the company Croda under the name Span 60, sorbitan tristearate, sold by the company Croda under the name Span 65 V, sorbitan monopalmitate (CTFA name: Sorbitan palmitate), sold by the company Croda under the name Span 40, sorbitan monooleate, sold by the company Croda under the name Span 80 V, and sorbitan trioleate, sold by the company Uniqema under the name Span 85 V. Preferably, the sorbitan ester used is sorbitan tristearate.

The fatty acid esters of sucrose are preferably chosen from esters derived from the reaction of sucrose(s) (saccharose) and of fatty acid(s) comprising from 10 to 24 carbon atoms, preferably from 12 to 20 carbon atoms, better still from 12 to 18 carbon atoms and even better still from 12 to 16 carbon atoms.

The fatty acids containing from 10 to 24 carbon atoms may be linear or branched, and saturated or unsaturated.

The fatty acids may be chosen from oleic acid, lauric acid, palmitic acid, myristic acid, stearic acid, linoleic acid and capric acid, or mixtures thereof.

According to one embodiment, the fatty acid ester of sucrose is chosen from esters derived from the reaction of sucrose and a fatty acid containing from 12 to 18 carbon atoms and preferably from 12 to 16 carbon atoms, such as lauric acid and/or palmitic acid, for instance sucrose laurate or sucrose palmitate, or a mixture thereof.

The fatty acid esters of sucrose may be chosen from mono-, di-, tri- and tetra-esters, and polyesters, and mixtures thereof. Esters with a low degree of esterification are preferably used, for instance fatty acid monoesters, diesters or triesters of sucrose, or a mixture thereof. The fatty acid ester of sucrose may be in the form of a mixture of esters with a low degree of esterification, for instance a mixture of monoester and diester or a mixture of monoester, diester and triester. In the case where use is made of a mixture of fatty acid esters of sucrose, preference is given to a mixture in which esters having a low degree of esterification, in particular the monoesters, are predominant and represent, for example, at least 50% by weight, preferably at least 60% by weight, of the mixture of fatty acid esters of sucrose.

Use may in particular be made of a mixture of esters of sucrose and of fatty acids comprising from 12 to 16 carbon atoms, in particular a mixture of mono-, di- and triesters of lauric acid or palmitic acid, it being possible for said mixture to comprise a minor amount (in a content of less than or equal to 40% by weight, relative to the weight of the mixture of fatty acid esters of sucrose) of fatty acid esters of sucrose in which the fatty acid comprises more than 16 carbon atoms.

Preferably, the fatty acid ester of sucrose used in the present invention has an HLB value of greater than or equal to 10, preferably of greater than or equal to 12. As is well known, the term HLB (Hydrophilic-Lipophilic Balance) means the equilibrium between the size and strength of the hydrophilic group and the size and strength of the lipophilic group of the surfactant.

The HLB value according to Griffin is defined in J. Soc. Cosm. Chem. 1954 (volume 5), pages 249-256.

Examples of esters or mixtures of esters of sucrose and of fatty acid that may be mentioned include:

Surfhope SE Cosme C-1416, with an HLB value of 16, which is a sucrose myristate comprising about 80% monoester, the rest of the mixture being composed of di- and triesters, Surfhope SE Cosme C-1216, the INCI name of which is sucrose laurate, with an HLB value of 16, and which comprises from 75% to 90% monoester, the rest of the mixture being composed of di- and triesters, Surfhope SE Cosme C-1215L, the INCI name of which is sucrose laurate, with an HLB value equal to 15, comprising about 70% monoesters, the rest of the mixture being composed of diesters and other polyesters, Surfhope SE Cosme C-1616, with an HLB value of 16, which is a mixture of esters of sucrose and of palmitic and/or stearic acid (INCI name: sucrose palmitate), comprising from 75% to 90% monoester, the rest of the mixture being composed of di- and triesters, and possibly comprising sucrose stearate and sucrose palmitate stearate.

Mention may also be made of the ester whose INCI name is sucrose laurate sold by the company Dai-ichi Seiyaku under the reference DK ester S-L18A, with an HLB equal to 17, comprising 70% monoesters and 30% diesters and triesters.

As examples of esters or mixtures of esters of sucrose and of fatty acid, mention may also be made of:

the products sold under the names F160, F140, F110, F90, F70 and SL40 by Crodesta, respectively denoting sucrose palmitate/stearates formed of 73% of monoester and 27% of di- and triester, of 61% of monoester and 39% of di-, tri-, and tetraester, of 52% of monoester and 48% of di-, tri-, and tetraester, of 45% of monoester and 55% of di-, tri- and tetraester, of 39% of monoester and 61% of di-, tri- and tetraester, and sucrose monolaurate;

the products sold under the name Ryoto Sugar Esters, for example referenced B370 and corresponding to the sucrose behenate formed of 20% of monoester and 80% of di-, tri- and polyester;

the sucrose mono-dipalmito-stearate sold by the company Goldschmidt under the name Tegosoft PSE.

According to one embodiment, sucrose laurate is used.

Among the nonionic surfactants according to the invention, mention may also be made of saponins.

The saponins may preferably be chosen from saponins extracted from soapnut trees (*Sapindus mukorossi, Sapindus trifoliatus, Sapindus saponaria*), liquorice (*Glycyrrhiza glabra*), horse chestnut (*Aesculus hippocastanum*), water hyssop (*Bacopa monnieri*), sarsaparilla (*Smilax medica, Smilax aspera, Smilax ornata*), Panama wood (*Quillaja saponaria*), common soapwort (*Saponaria officinalis*), ginseng (*Panax ginseng*), yucca (*Yucca schidigera*), puncture vine (*Tribulus terrestris*), juazeiro (*Ziziphus joazeiro*), jiaogulan (*Gynostemma pentaphyllum*), Indian asparagus (*Asparagus racemosus*) and alfalfa (*Medicago sativa*), and mixtures thereof.

Preferably, the nonionic surfactant is chosen from the group formed by alkylpolyglucosides, alkylglycosides, polyols, sugar esters, ethoxylated alcohols, and polyoxyethylene fatty acid esters of sorbitan, and mixtures thereof.

According to one embodiment, the surfactant is a nonionic surfactant chosen from the group formed by decyl glucoside, cocoyl glucoside, sucrose laurate, sorbitol, and polyoxyethylene sorbitan monolaurate (Polysorbate 20), and mixtures thereof.

According to one embodiment, the surfactant is decyl glucoside or cocoyl glucoside.

According to one embodiment, the surfactant is a mixture of sucrose laurate and sorbitol.

According to another embodiment, the surfactant is polyoxyethylene sorbitan monolaurate (Polysorbate 20).

The cosmetic compositions of the invention may comprise a single surfactant as defined above, or a mixture of surfactants as defined above.

In particular, the cosmetic compositions of the invention comprise a surfactant.

According to the invention, the total content of surfactant(s) (spiculisporic acid+additional surfactant) in the cosmetic composition of the invention may range from 0.1% to 30% by mass relative to the total mass of said composition.

Preferably, the total content of surfactant(s) (spiculisporic acid+additional surfactant) according to the invention ranges from 0.5% to 15% and preferentially from 1% to 10% by mass relative to the total mass of said composition.

According to a preferred embodiment, the total content of surfactant(s) (spiculisporic acid+additional surfactant) according to the invention is between 1% and 10% and preferably between 2% and 10%.

Base

Thus, the compositions according to the invention, preferably cosmetic compositions, in which spiculisporic acid is included may also comprise an organic or mineral base. The organic or mineral base may be a Brønsted-Lowry base or a Lewis base.

In particular, the base(s) may be chosen from:

a) alkanolamines such as mono-, di- and triethanolamines, isopropanolamine and 2-amino-2-methyl-1-propanol, and also derivatives thereof, b) oxyethylenated and/or oxypropylenated ethylenediamines, c) mineral or organic hydroxides, d) alkali metal silicates such as sodium metasilicates, e) amino acids, preferably basic amino acids such as arginine, lysine, ornithine, citrulline and histidine, f) carbonates and bicarbonates, particularly of a primary, secondary or tertiary amine, of an alkali metal or alkaline-earth metal, or of ammonium, and g) the compounds of formula (III) below:

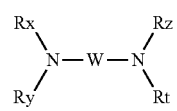

(III)

in which W is a C1-C6 alkylene residue optionally substituted with a hydroxyl group or a C1-C6 alkyl group; Rx, Ry, Rz and Rt, which may be identical or different, represent a hydrogen atom or a C1-C6 alkyl, C1-C6 hydroxyalkyl or C1-C6 aminoalkyl group.

Examples of such compounds of formula (III) that may be mentioned include 1,3-diaminopropane, 1,3-diamino-2-propanol, spermine and spermidine.

The mineral or organic hydroxides are preferably chosen from hydroxides of an alkali metal, hydroxides of an alkaline-earth metal, for instance sodium hydroxide or potassium hydroxide, hydroxides of a transition metal, such as hydroxides of metals from Groups III, IV, V and VI of the Periodic Table of the Elements, hydroxides of lanthanides or actinides, quaternary ammonium hydroxides and guanidinium hydroxide.

The hydroxide may be formed in situ, for instance guanidine hydroxide, formed by reacting calcium hydroxide and guanidine carbonate.

According to a particular embodiment of the invention, the base may be chosen from the group of mineral bases such as sodium hydroxide, potassium hydroxide, lithium hydroxide, cesium hydroxide, calcium hydroxide, magnesium hydroxide, zinc hydroxide, or similar bases, a basic mineral salt and a basic organic salt containing lithium, sodium, potassium, calcium, magnesium or ammonium, a basic amino acid such as lysine, arginine, histidine, ornithine or the like, a basic oligopeptide containing these amino acids as bases, basic amines such as monoethanolamine, diethanolamine, 2-(dimethylamino)ethanol, triethanolamine, triisopropanolamine, diisopropanolamine, monoisopropanolamine, ammonia, or similar bases, or other organic bases such as guanidine carbonate and other similar bases, and mixtures thereof.

According to one embodiment, the base is potassium hydroxide.

According to one embodiment, the base is arginine.

In the context of the invention, and unless otherwise mentioned, the base used is a neutralizing base, i.e. it enables the spiculisporic acid to be neutralized so as to form a salt of said acid. Examples that may be mentioned include the sodium, potassium, triethanolamine and arginine salts of spiculisporic acid.

According to one embodiment, the use of two moles of spiculisporic acid can neutralize two carboxylic functions of said acid without breaking the lactone function. In particular, two moles of base are used per one mole of spiculisporic acid in the abovementioned cosmetic compositions.

According to one embodiment, the use of potassium hydroxide allows the formation of the monopotassium salt, the dipotassium salt or the tripotassium salt of spiculisporic acid.

The composition, preferably the cosmetic, deodorant composition may also comprise, besides spiculisporic acid as defined previously, at least one additional deodorant active agent and/or one antiperspirant active agent as defined below.

Deodorant Active Agents

The deodorant active agents may be bacteriostatic agents or bactericides that act on underarm odor microorganisms, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts, polyols such as those of glycerol type, 1,3-propanediol (Zemea Propanediol® sold by DuPont Tate & Lyle Bio Products), 1,2-decanediol (Symclariol® from the company Symrise), glycerol derivatives, for instance caprylic/capric glycerides (Capmul MCM® from Abitec), glyceryl caprylate or caprate (Dermosoft GMCY® and Dermosoft GMC®, respectively from Straetmans), Polyglyceryl-2 caprate (Dermosoft DGMC® from Straetmans), biguanide derivatives, for instance polyhexamethylene biguanide salts; chlorhexidine and salts thereof; 4-phenyl-4,4-dimethyl-2-butanol (Symdeo MPP® from Symrise); cyclodextrins; chelating agents such as Tetrasodium Glutamate Diacetate (CAS #51981-21-6) sold under the trade name Dissolvine GL-47-S® from AkzoNobel, EDTA (ethylenediaminetetraacetic acid) and DPTA (1,3-diaminopropanetetraacetic acid).

Among the deodorant active agents in accordance with the invention, mention may also be made of:

zinc salts, such as zinc salicylate, zinc phenolsulfonate, zinc pyrrolidonecarboxylate (more commonly known as zinc pidolate), zinc sulfate, zinc chloride, zinc lactate, zinc gluconate, zinc ricinoleate, zinc glycinate, zinc carbonate, zinc citrate, zinc chloride, zinc laurate, zinc oleate, zinc orthophosphate, zinc stearate, zinc tartrate, zinc acetate or mixtures thereof;

odor absorbers such as zeolites, especially silver-free metal zeolites, cyclodextrins, metal oxide silicates such as those described in patent application US 2005/063 928; metal oxide particles modified with a transition metal, as described in patent applications US 2005/084 464 and US 2005/084 474, aluminosilicates such as those described in patent application EP 1 658 863, chitosan-based particles such as those described in U.S. Pat. No. 6,916,465;

sodium bicarbonate;

salicylic acid and derivatives thereof such as 5-n-octanoylsalicylic acid;

alum;

triethyl citrate;

and mixtures thereof.

The additional deodorant active agents may be present in the composition according to the invention in a proportion of from 0.01% to 10% by weight and preferably in a proportion of from 0.1% to 5% by weight relative to the total weight of the composition.

Antiperspirant Active Agents

Among the antiperspirant active agents, mention may be made of the antiperspirant salts or complexes of aluminum and/or of zirconium, preferably chosen from aluminum halohydrates; aluminum zirconium halohydrates, complexes of zirconium hydroxychloride and of aluminum hydroxychloride with or without an amino acid, such as those described in U.S. Pat. No. 3,792,068.

Among the aluminum salts, mention may in particular be made of aluminum chlorohydrate in activated or unactivated form, aluminum chlorohydrex, the aluminum chlorohydrex-polyethylene glycol complex, the aluminum chlorohydrex-propylene glycol complex, aluminum dichlorohydrate, the aluminum dichlorohydrex-polyethylene glycol complex, the aluminum dichlorohydrex-propylene glycol complex, aluminum sesquichlorohydrate, the aluminum sesquichlorohydrex-polyethylene glycol complex, the aluminum sesquichlorohydrex-propylene glycol complex, aluminum sulfate buffered with sodium aluminum lactate.

Among the aluminum zirconium salts, mention may be made in particular of aluminum zirconium octachlorohydrate, aluminum zirconium pentachlorohydrate, aluminum zirconium tetrachlorohydrate and aluminum zirconium trichlorohydrate.

The complexes of zirconium hydroxychloride and of aluminum hydroxychloride with an amino acid are generally known under the name ZAG (when the amino acid is glycine). Among these products, mention may be made of the aluminum zirconium octachlorohydrex-glycine complexes, the aluminum zirconium pentachlorohydrex-glycine complexes, the aluminum zirconium tetrachlorohydrex-glycine complexes and the aluminum zirconium trichlorohydrex-glycine complexes.

Aluminum sesquichlorohydrate is in particular sold under the trade name Reach 301® by the company Summitreheis.

Among the aluminum and zirconium complexes, mention may be made of the complexes of zirconium hydroxychloride and of aluminum hydroxychloride with an amino acid such as glycine, having the INCI name: Aluminium Zirconium Tetrachlorohydrex Gly, for example the product sold under the name Reach AZP-908-SUF® by the company Summitreheis.

Use will be made more particularly of aluminum chlorohydrate in activated or unactivated form sold under the trade names Locron S FLA®, Locron P and Locron L.ZA by the company Clariant; under the trade names Microdry Aluminum Chlorohydrate®, Micro-Dry 323®, Chlorhydrol 50, Reach 103 and Reach 501 by the company Summitreheis; under the trade name Westchlor 200® by the company Westwood; under the trade name Aloxicoll PF 40® by the company Guilini Chemie; Cluron 50%® by the company Industria Quimica Del Centro; or Clorohidroxido Aluminio SO A 50%® by the company Finquimica.

As other antiperspirant active agent, mention may be made of expanded perlite particles such as those obtained by the expansion process described in U.S. Pat. No. 5,002,698.

The perlites that may be used according to the invention are generally aluminosilicates of volcanic origin and have the composition:

70.0-75.0% by weight of silica SiO2
12.0-15.0% by weight of oxide of aluminum oxide Al2O3
3.0-5.0% of sodium oxide Na2O
3.0-5.0% of potassium oxide K2O
0.5-2% of iron oxide Fe2O3
0.2-0.7% of magnesium oxide MgO
0.5-1.5% of calcium oxide CaO
0.05-0.15% of titanium oxide TiO2.

Preferably, the perlite particles used will be ground; in this case, they are known as Expanded Milled Perlite (EMP). They preferably have a particle size defined by a median diameter D50 ranging from 0.5 to 50 µm and preferably from 0.5 to 40 µm.

Preferably, the perlite particles used have a loose bulk density at 25° C. ranging from 10 to 400 kg/m$^3$ (standard DIN 53468) and preferably from 10 to 300 kg/m$^3$.

Preferably, the expanded perlite particles according to the invention have a water absorption capacity, measured at the wet point, ranging from 200% to 1500% and preferably from 250% to 800%.

The wet point corresponds to the amount of water which has to be added to 1 g of particle in order to obtain a homogeneous paste. This method is directly derived from the oil uptake method applied to solvents. The measurements are taken in the same manner by means of the wet point and the flow point, which have, respectively, the following definitions:

Wet point: weight, expressed in grams per 100 g of product, corresponding to the production of a homogeneous paste during the addition of a solvent to a powder.

Flow point: mass expressed in grams per 100 g of product from which the amount of solvent is greater than the capacity of the powder to retain it. This is reflected by the production of a more or less homogeneous mixture which flows over the glass plate.

The wet point and the flow point are measured according to the following protocol: Protocol for measuring the water absorption 1) Equipment Used
Glass plate (25×25 mm)
Spatula (wooden shaft and metal part, 15×2.7 mm)
Silk-bristled brush
Balance
2) Procedure The glass plate is placed on the balance and 1 g of perlite particles is weighed out. The beaker containing the solvent and the liquid sampling pipette is placed on the balance. The solvent is gradually added to the powder, the whole being regularly blended (every 3 to 4 drops) by means of the spatula.

The mass of solvent needed to obtain the wet point is noted. Further solvent is added and the mass which makes it possible to reach the flow point is noted. The average of three tests will be determined.

The expanded perlite particles sold under the trade names Optimat 1430 OR or Optimat 2550 by the company World Minerals will be used in particular.

The antiperspirant active agents may be present in the composition according to the invention in a proportion of from 0.001% to 30% by weight, and preferably in a proportion of from 0.5% to 25% by weight, relative to the total weight of the composition.

Presentation Forms

The composition according to the invention may be in any presentation form conventionally used for topical application and especially in the form of aqueous gels, or aqueous or aqueous-alcoholic solutions. By adding a fatty or oily phase, it may also be in the form of dispersions of lotion type, emulsions of liquid or semi-liquid consistency of milk type, obtained by dispersing a fatty phase in an aqueous phase (O/W) or conversely (W/O), or suspensions or emulsions of soft, semi-solid or solid consistency of the cream or gel type, or alternatively multiple emulsions (W/O/W or O/W/O), microemulsions, vesicular dispersions of ionic and/or nonionic type, or wax/aqueous phase dispersions. These compositions are prepared according to the usual methods.

The compositions may especially be conditioned in pressurized form in an aerosol device or in a pump-action bottle; conditioned in a device equipped with an openwork wall, especially a grate; conditioned in a device equipped with a ball applicator ("roll-on"); conditioned in the form of wands (sticks) or in the form of loose or compacted powder. In this regard, they comprise the ingredients generally used in products of this type, which are well known to those skilled in the art.

In a particular embodiment, the invention relates to a composition as defined previously comprising spiculisporic acid in free form or in a form partially neutralized or totally neutralized with at least one mineral base and/or one organic base, characterized in that it is in the form of aqueous gels; of an aqueous or aqueous-alcoholic solution, of a simple or multiple emulsion, of a vesicular dispersion of ionic and/or nonionic type, or of a wax/aqueous phase dispersion.

According to another particular form of the invention, the compositions according to the invention may be anhydrous.

The term "anhydrous composition" means a composition containing less than 2% by weight of water, or even less than 0.5% of water, and especially free of water, the water not being added during the preparation of the composition but corresponding to the residual water provided by the mixed ingredients.

According to another particular form of the invention, the compositions according to the invention may be solid, in particular in wand or stick form.

The term "solid composition" means that the measurement of the maximum force measured by texturometry during the penetration of a probe into the sample of formulation must be at least equal to 0.25 newton, in particular at least equal to 0.30 newton and especially at least equal to 0.35 newton, assessed under precise measurement conditions as follows.

The formulations are poured hot into jars 4 cm in diameter and 3 cm deep. Cooling is performed at room temperature.

The hardness of the formulations produced is measured after an interval of 24 hours. The jars containing the samples are characterized in texturometry using a texturometer such as the machine sold by the company Rheo TA-XT2, according to the following protocol: a stainless-steel ball probe 5 mm in diameter is brought into contact with the sample at a speed of 1 mm/s. The measurement system detects the interface with the sample, with a detection threshold equal to 0.005 newton. The probe penetrates 0.3 mm into the sample, at a speed of 0.1 mm/s. The measuring machine records the change in force measured in compression over time, during the penetration phase. The hardness of the sample corresponds to the average of the maximum force values detected during penetration, over at least three measurements.

Physiologically Acceptable Medium

A composition according to the invention may be a cosmetic, dermatological, or pharmaceutical composition, preferably cosmetic.

A composition according to the invention especially comprises a physiologically acceptable medium.

In the context of the invention, and unless otherwise mentioned, the term "physiologically acceptable medium" means a medium that is suitable for cosmetic uses, and is especially suitable for applying a composition of the invention to the skin and/or the hair. The physiologically acceptable medium is generally adapted to the nature of the support onto which the composition has to be applied, and also to the appearance under which the composition has to be packaged.

Aqueous Phase

The compositions according to the invention intended for cosmetic use may comprise at least one aqueous phase. They are in particular formulated as aqueous lotions or as water-in-oil or oil-in-water emulsions or as multiple emulsions (oil-in-water-in-oil or water-in-oil-in-water triple emulsions (such emulsions are known and described, for example, by C. Fox in "Cosmetics and Toiletries"—November 1986—Vol. 101—pages 101-112)).

The aqueous phase of said compositions contains water and generally other water-soluble or water-miscible solvents. The water-soluble or water-miscible solvents comprise short-chain, for example $C_1$-$C_4$, monoalcohols, such as ethanol or isopropanol; diols or polyols, such as ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Propylene glycol and glycerol, propane-1,3-diol, will be used more particularly.

According to the invention, the pH of the composition according to the invention may be between 3 and 10. Preferably, the pH is between 5 and 8 and in particular between 5 and 6.5.

Emulsifiers

Oil-in-Water Emulsifiers

As emulsifiers that may be used in the oil-in-water emulsions or oil-in-water-in-oil triple emulsions, examples that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof, such as the mixture of glyceryl stearate and PEG-40 stearate.

Mention may also be made of fatty alcohol/alkylpolyglycoside emulsifying mixtures as described in patent applications WO 92/06778, WO 95/13863 and WO 98/47610, for instance the commercial products sold by the company SEPPIC under the name Montanov®.

Water-in-Oil Emulsifiers

Among the emulsifiers that may be used in the water-in-oil emulsions or water-in-oil-in-water-in-oil triple emulsions or triple emulsions, examples that may be mentioned include alkyl dimethicone copolyols, for instance Cetyl PEG/PPG-10/1 Dimethicone and more particularly the mixture Cetyl PEG/PPG-10/1 Dimethicone and Dimethicone (INCI name), such as the product sold under the trade name Abil EM90 by the company Goldschmidt, or alternatively the mixture (Polyglyceryl-4 stearate and Cetyl PEG/PPG-10 (and) Dimethicone (and) Hexyl Laurate), such as the product sold under the trade name Abil WE09 by the same company.

Among the water-in-oil emulsifiers, mention may also be made of dimethicone copolyols, for instance PEG-18/PPG-18 Dimethicone and more particularly the mixture Cyclopentasiloxane (and) PEG-18/PPG-18 Dimethicone (INCI name), such as the product sold by the company Dow Corning under the trade name Silicone DC 5225 C or KF-6040 from the company Shin-Etsu.

Among the water-in-oil emulsifiers, mention may also be made of nonionic emulsifiers derived from fatty acids and polyols, alkyl polyglycosides (APGs) and sugar esters, and mixtures thereof.

As nonionic emulsifiers derived from fatty acids and polyols, use may be made especially of fatty acid esters of polyols, the fatty acid especially containing a C8-C24 alkyl chain, and the polyols being, for example, glycerol and sorbitan.

Fatty acid esters of polyols that may especially be mentioned include isostearic acid esters of polyols, stearic acid esters of polyols, and mixtures thereof, in particular isostearic acid esters of glycerol and/or sorbitan.

Stearic acid esters of polyols that may especially be mentioned include the polyethylene glycol esters, for instance PEG-30 dipolyhydroxystearate, such as the product sold under the name Arlacel P135 by the company ICI.

Examples of glycerol and/or sorbitan esters that may be mentioned include polyglyceryl isostearate, such as the product sold under the name Isolan GI 34 by the company Goldschmidt; sorbitan isostearate, such as the product sold under the name Arlacel 987 by the company ICI; sorbitan glyceryl isostearate, such as the product sold under the name Arlacel 986 by the company ICI, the mixture of sorbitan isostearate and polyglyceryl isostearate (3 mol) sold under the name Arlacel 1690 by the company Uniqema, and mixtures thereof.

The emulsifier may also be chosen from alkylpolyglycosides with an HLB of less than 7, for example those represented by the general formula (1) below:

$$R\text{—}O\text{-}(G)_x \qquad (1)$$

in which R represents a branched and/or unsaturated alkyl radical comprising from 14 to 24 carbon atoms, G represents a reduced sugar comprising 5 or 6 carbon atoms, and x is a value ranging from 1 to 10 and preferably from 1 to 4, and G especially denotes glucose, fructose or galactose.

The unsaturated alkyl radical may comprise one or more ethylenically unsaturated groups, and in particular one or two ethylenically unsaturated groups.

As alkylpolyglycosides of this type, mention may be made of alkylpolyglucosides (G=glucose in formula (I)), and especially the compounds of formula (I) in which R more particularly represents an oleyl radical (unsaturated C18 radical) or isostearyl (saturated C18 radical), G denotes glucose, x is a value ranging from 1 to 2, especially isostearyl-glucoside or oleyl-glucoside, and mixtures thereof. This alkyl polyglucoside may be used as a mixture with a coemulsifier, more especially with a fatty alcohol and especially a fatty alcohol containing the same fatty chain as that of the alkyl polyglucoside, i.e. comprising from 14 to 24 carbon atoms and containing a branched and/or unsaturated chain, for example isostearyl alcohol when the alkyl polyglucoside is isostearyl glucoside, and oleyl alcohol when the alkyl polyglucoside is oleyl glucoside, optionally in the form of a self-emulsifying composition, as described, for example, in document WO-A-92/06778. Use may be made, for example, of the mixture of isostearyl glucoside and isostearyl alcohol, sold under the name Montanov WO 18 by the company SEPPIC, and also the mixture octyldodecanol and octyldodecyl xyloside sold under the name Fludanov 20X by the company SEPPIC.

Mention may also be made of succinic-terminated polyolefins, for instance esterified succinic-terminated polyisobutylenes and salts thereof, especially the diethanolamine salts, such as the products sold under the names Lubrizol 2724, Lubrizol 2722 and Lubrizol 5603 by the company Lubrizol or the commercial product Chemcinnate 2000.

The total amount of emulsifiers in the composition will preferably be, in the composition according to the invention, in active material contents ranging from 1% to 8% by weight and more particularly from 2% to 6% by weight relative to the total weight of the composition.

Fatty Phase

The compositions according to the invention may contain at least one water-immiscible organic liquid phase, known as a fatty phase. This phase generally comprises one or more hydrophobic compounds which render said phase water-immiscible. Said phase is liquid (in the absence of structuring agent) at room temperature (20-25° C.). Preferentially, the water-immiscible organic liquid phase in accordance with the invention generally comprises at least one volatile oil and/or nonvolatile oil and optionally at least one structuring agent.

The term "oil" means a fatty substance that is liquid at room temperature (25° C.) and atmospheric pressure (760 mmHg, i.e. 105 Pa). The oil may be volatile or nonvolatile.

For the purposes of the invention, the term "volatile oil" means an oil that is capable of evaporating on contact with the skin or the keratin fiber in less than one hour, at room temperature and atmospheric pressure. The volatile oils of the invention are volatile cosmetic oils which are liquid at room temperature, with a nonzero vapor pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "nonvolatile oil" means an oil that remains on the skin or the keratin fiber at room temperature and atmospheric pressure for at least several hours, and that especially has a vapor pressure of less than $10^{-3}$ mmHg (0.13 Pa).

The oil may be chosen from any physiologically acceptable oil and in particular cosmetically acceptable oil, especially mineral, animal, plant or synthetic oils; in particular volatile or nonvolatile hydrocarbon-based oils and/or silicone oils and/or fluoro oils, and mixtures thereof.

More precisely, the term "hydrocarbon-based oil" means an oil mainly comprising carbon and hydrogen atoms and optionally one or more functions chosen from hydroxyl, ester, ether and carboxylic functions. Generally, the oil has a viscosity of from 0.5 to 100 000 mPa·s, preferably from 50 to 50 000 mPa·s and more preferably from 100 to 300 000 mPa·s.

As examples of volatile oils that may be used in the invention, mention may be made of:

volatile hydrocarbon-based oils chosen from hydrocarbon-based oils containing from 8 to 16 carbon atoms, and especially $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_8$-$C_{16}$ esters and isohexyl neopentanoate, and mixtures thereof. Use may also be made of other volatile hydrocarbon-based oils, such as petroleum distillates, in particular those sold under the name Shell Solt by the company Shell; and volatile linear alkanes, such as those described in patent application DE10 2008 012 457 from the company Cognis;

volatile silicones, for instance linear or cyclic volatile silicone oils, in particular those with a viscosity of ≤8 centistokes ($8\times10^{-6}$ m$^2$/s), and containing in particular from 2 to 7 silicon atoms, these silicones optionally comprising alkyl or alkoxy groups containing from 1 to 10 carbon atoms. As volatile silicone oil that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane;

and mixtures thereof.

Mention may also be made of the volatile linear alkyltrisiloxane oils of general formula (I):

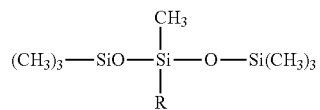

where R represents an alkyl group comprising from 2 to 4 carbon atoms, one or more hydrogen atoms of which may be replaced with a fluorine or chlorine atom.

Among the oils of general formula (I), mention may be made of:

3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

As examples of nonvolatile oils that may be used in the invention, mention may be made of:

hydrocarbon-based oils of animal origin, such as perhydrosqualene;

hydrocarbon-based plant oils such as liquid triglycerides of fatty acids having 4 to 24 carbon atoms, for instance heptanoic or octanoic acid triglycerides, or else wheatgerm oil, olive oil, sweet almond oil, palm oil, rapeseed oil, cottonseed oil, alfalfa oil, poppy oil, pumpkin oil, marrow oil, blackcurrant oil, evening primrose oil, millet oil, barley oil, *quinoa* oil, rye oil, safflower oil, candlenut oil, passionflower oil, musk rose oil, sunflower oil, corn oil, soybean oil, marrow oil, grapeseed oil, sesame seed oil, hazelnut oil, apricot oil, macadamia oil, castor oil, avocado oil, caprylic/capric acid triglycerides, for instance those sold by the company Stéarineries Dubois or those sold under the names Miglyol 810, 812 and 818 by the company Dynamit Nobel, jojoba oil and shea butter oil;

linear or branched hydrocarbons, of mineral or synthetic origin, such as liquid paraffins and derivatives thereof, petroleum jelly, polydecenes, polybutenes, hydrogenated polyisobutene such as Parleam, or squalane;

synthetic ethers containing from 10 to 40 carbon atoms;

synthetic esters, in particular of fatty acids, for instance the oils of formula $R_1COOR_2$ in which $R_1$ represents the residue of a linear or branched higher fatty acid containing from 1 to 40 carbon atoms and $R_2$ represents a hydrocarbon-based chain, which is in particular branched, containing from 1 to 40 carbon atoms, with $R_1+R_2 \geq 10$, for instance purcellin oil (cetostearyl octanoate), isononyl isononanoate, isopropyl myristate, isopropyl palmitate, $C_{12}$ to $C_{15}$ alkyl benzoate, hexyl laurate, diisopropyl adipate, isononyl isononanoate, 2-ethylhexyl palmitate, 2-octyldodecyl stearate, 2-octyldodecyl erucate, isostearyl isostearate or tridecyl trimellitate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetraisostearate;

fatty alcohols which are liquid at room temperature, comprising a branched and/or unsaturated carbon chain having from 12 to 26 carbon atoms, such as octyldodecanol, isostearyl alcohol, 2-butyloctanol, 2-hexyldecanol, 2-undecylpentadecanol or oleyl alcohol;

higher fatty acids, such as oleic acid, linoleic acid or linolenic acid;

carbonates;

acetates;

citrates;

fluorinated oils which are optionally partially hydrocarbon-based and/or silicone-based, for instance fluorosilicone oils, fluorinated polyethers or fluorinated silicones, such as described in the document EP-A-847 752;

silicone oils, for instance nonvolatile linear or cyclic polydimethylsiloxanes (PDMSs); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates, and mixtures thereof.

Additives

The cosmetic compositions according to the invention may also comprise cosmetic adjuvants chosen from emollients, antioxidants, opacifiers, stabilizers, moisturizers, vitamins, bactericides, preserving agents, polymers, fragrances, a structuring agent for a fatty phase, in particular chosen from waxes, pasty compounds, mineral or organic lipophilic gelling agents; organic or mineral fillers; thickeners or suspending agents, propellants or any other ingredient normally used in cosmetics for this type of application.

Needless to say, a person skilled in the art will take care to select this or these optional additional compounds such that the advantageous properties intrinsically associated with the cosmetic composition in accordance with the invention are not, or are not substantially, adversely affected by the envisaged addition(s).

Wax(es)

The wax is in general a lipophilic compound that is solid at room temperature (25° C.), with a reversible solid/liquid change in state, having a melting point of greater than or equal to 30° C., which may be up to 200° C. and in particular up to 120° C.

In particular, the waxes that are suitable for use in the invention may have a melting point of greater than or equal to 45° C. and in particular greater than or equal to 55° C.

Within the meaning of the invention, the melting point corresponds to the temperature of the most endothermic peak observed in thermal analysis (DSC) as described in Standard ISO 11357-3: 1999. The melting point of the wax may be measured using a differential scanning calorimeter (DSC), for example the calorimeter sold under the name MDSC 2920 by the company TA Instruments.

The measurement protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes that may be used in the compositions according to the invention are chosen from waxes that are solid at room temperature, of animal, plant, mineral or synthetic origin, and mixtures thereof.

As illustrations of waxes that are suitable for use in the invention, mention may be made especially of hydrocarbon-based waxes, for instance beeswax, lanolin wax, Chinese insect waxes, rice bran wax, carnauba wax, candelilla wax, ouricury wax, esparto grass wax, berry wax, shellac wax, Japan wax and sumach wax; montan wax, orange wax and lemon wax, refined sunflower wax sold under the name Sunflower Wax by Koster Keunen, microcrystalline waxes, paraffins and ozokerite; polyethylene waxes, the waxes obtained by Fischer-Tropsch synthesis and waxy copolymers, and also esters thereof.

Mention may also be made of waxes obtained by catalytic hydrogenation of animal or plant oils containing linear or branched C8-C32 fatty chains. Mention may especially be made, among these waxes, of isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate sold under the name Hest 2T-4S® by the company Heterene.

Mention may also be made of silicone waxes ($C_{30-45}$ alkyl dimethicone) and fluoro waxes.

The waxes obtained by hydrogenation of castor oil esterified with cetyl alcohol, sold under the names Phytowax ricin 16L64® and 22L73® by the company Sophim, may also be used. Such waxes are described in patent application FR-A-2 792 190.

As wax, use may be made of a C20-C40 alkyl (hydroxystearyloxy)stearate (the alkyl group comprising from 20 to 40 carbon atoms), alone or as a mixture.

Such a wax is especially sold under the names "Kester Wax K 82 P®", "Hydroxypolyester K 82 P®" and "Kester Wax K 80 P®" by the company Koster Keunen.

As microwaxes that may be used in the compositions according to the invention, mention may be made especially of carnauba microwaxes, such as the product sold under the name MicroCare 350® by the company Micro Powders, synthetic microwaxes, such as the product sold under the name MicroEase 114S® by the company Micro Powders, microwaxes formed from a mixture of carnauba wax and polyethylene wax, such as the products sold under the names Micro Care 300® and 310® by the company Micro Powders, microwaxes formed from a mixture of carnauba wax and of synthetic wax, such as the product sold under the name Micro Care 325® by the company Micro Powders, polyethylene microwaxes, such as the products sold under the names Micropoly 200®, 220®, 220L® and 250S® by the company Micro Powders, the commercial products Performalene 400, Polyethylene and Performalene 500-L, Polyethylene from New Phase Technologies, Performalene 655, Polyethylene or paraffin waxes, for instance the wax having the INCI name Microcrystalline Wax and Synthetic Wax and sold under the trade name Microlease by the company Sochibo; polytetrafluoroethylene microwaxes such as those sold under the names Microslip 519® and 519 L® by the company Micro Powders.

Pasty Compounds

For the purposes of the present invention, the term "pasty compound" means a lipophilic fatty compound with a reversible solid/liquid change of state, having in the solid state an anisotropic crystal organization, and comprising at a temperature of 23° C. a liquid fraction and a solid fraction.

The pasty compound is preferably chosen from synthetic compounds and compounds of plant origin. A pasty compound may be obtained via synthesis from starting materials of plant origin.

The pasty compound may be advantageously chosen from:
lanolin and derivatives thereof,
polymeric or non-polymeric silicone compounds,
polymeric or non-polymeric fluorinated compounds,
vinyl polymers, in particular:
olefin homopolymers,
olefin copolymers,
hydrogenated diene homopolymers and copolymers,
linear or branched homopolymer or copolymer oligomers of alkyl (meth)acrylates preferably containing a $C_8$-$C_{30}$ alkyl group,
homopolymeric and copolymeric oligomers of vinyl esters containing $C_8$-$C_{30}$ alkyl groups, and
homopolymeric and copolymeric oligomers of vinyl ethers containing $C_8$-$C_{30}$ alkyl groups,
liposoluble polyethers resulting from the polyetherification between one or more $C_2$-$C_{100}$ and preferably $C_2$-$C_{50}$ diols,
esters,
mixtures thereof.

Among the esters, the following are especially preferred:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as those sold under the brand name Softisan 649 by the company Sasol,
the arachidyl propionate sold under the brand name Waxenol 801 by Alzo,
phytosterol esters,
fatty acid triglycerides and derivatives thereof,
pentaerythritol esters,
non-crosslinked polyesters resulting from polycondensation between a linear or branched $C_4$-$C_{50}$ dicarboxylic acid or polycarboxylic acid and a $C_2$-$C_{50}$ diol or polyol,
ester aliphatic esters resulting from the esterification of an aliphatic hydroxycarboxylic acid ester with an aliphatic carboxylic acid,
polyesters resulting from the esterification, with a polycarboxylic acid, of an aliphatic hydroxycarboxylic acid ester, said ester comprising at least two hydroxyl groups, such as the products Risocast DA-H® and Risocast DA-L®,
esters of a diol dimer and of a diacid dimer, where appropriate esterified on their free alcohol or acid functional group(s) by acid or alcohol radicals, such as Plandool-G,
mixtures thereof.

Mineral Lipophilic Gelling Agents

Mineral lipophilic gelling agents that may be mentioned include optionally modified clays, for instance hectorites modified with a $C_{10}$ to $C_{22}$ ammonium chloride, for instance hectorite modified with distearyldimethylammonium chloride, for instance the product sold under the name Bentone 38V® by the company Elementis.

Mention may also be made of fumed silica optionally hydrophobically treated at the surface, the size of the particles of which is less than 1 µm. This is because it is possible to chemically modify the surface of the silica, by chemical reaction generating a reduction in the number of silanol groups present at the surface of the silica. It is especially possible to substitute silanol groups with hydrophobic groups: a hydrophobic silica is then obtained. The hydrophobic groups may be trimethylsiloxyl groups, which are obtained especially by treating fumed silica in the presence of hexamethyldisilazane. Silicas thus treated are known as "silica silylate" according to the CTFA (8th Edition, 2000). They are sold, for example, under the references Aerosil R812® by the company Degussa, CAB-O-SIL TS-530® by the company Cabot, dimethylsilyloxyl or polydimethylsiloxane groups, which are obtained especially by treating fumed silica in the presence of polydimethylsiloxane or dimethyldichlorosilane. Silicas thus treated are known as "silica dimethyl silylate" according to the CTFA (8th Edition, 2000). They are sold, for example, under the references Aerosil R972® and Aerosil R974® by the company Degussa and Cab-O-Sil TS-610® and Cab-O-Sil TS-720® by the company Cabot.

The hydrophobic fumed silica in particular has a particle size that may be nanometric to micrometric, for example ranging from about 5 to 200 nm.

Organic Lipophilic Gelling Agents

The polymeric organic lipophilic gelling agents are, for example, partially or totally crosslinked elastomeric organopolysiloxanes of three-dimensional structure, for instance those sold under the names KSG6®, KSG16® and KSG18® by the company Shin-Etsu, Trefil E-505C® and Trefil E-506C® by the company Dow Corning, Gransil SR-CYC®, SR DMF10®, SR-DC556®, SR 5CYC Gel®, SR DMF 10 Gel® and SR DC 556 Gel® by the company Grant Industries and SF 1204® and JK 113® by the company General Electric; ethylcellulose, for instance the product sold under the name Ethocel® by the company Dow Chemical; galactomannans comprising from one to six and in particular from two to four hydroxyl groups per monosaccharide, substituted with a saturated or unsaturated alkyl chain, for instance guar gum alkylated with $C_1$ to $C_6$, and in particular $C_1$ to $C_3$, alkyl chains, and mixtures thereof. Block copolymers of "diblock", "triblock" or "radial" type, of the polystyrene/polyisoprene or polystyrene/polybutadiene type, such as the products sold under the name Luvitol HSB® by the company BASF, of the polystyrene/copoly (ethylene-propylene) type, such as the products sold under the name Kraton® by the company Shell Chemical Co., or of the polystyrene/copoly(ethylene-butylene) type, and mixtures of triblock and radial (star) copolymers in isododecane, such as those sold by the company Penreco under the name Versagel®, for instance the mixture of butylene/ethylene/styrene triblock copolymer and of ethylene/propylene/styrene star copolymer in isododecane (Versagel M 5960).

Among the lipophilic gelling agents that may be used in the compositions according to the invention, mention may also be made of fatty acid esters of dextrin, such as dextrin palmitates, especially the products sold under the name Rheopearl TL® or Rheopearl KL® by the company Chiba Flour.

It is also possible to use silicone polyamides of the polyorganosiloxane type, such as those described in documents U.S. Pat. Nos. 5,874,069, 5,919,441, 6,051,216 and 5,981,680.

Thickeners and Suspending Agents

The thickeners may be chosen from carboxyvinyl polymers, such as Carbopols (Carbomers) and the Pemulens (acrylate/C10-C30 alkyl acrylate copolymer); polyacrylamides, for instance the crosslinked copolymers sold under the names Sepigel 305 (CTFA name: polyacrylamide/C13-14 isoparaffin/laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, optionally crosslinked and/or neutralized, for instance poly(2-acrylamido-2-methylpropanesulfonic acid) sold by the company Hoechst under the trade name Hostacerin AMPS (CTFA name: ammonium polyacryloyldimethyltaurate or Simulgel 800 sold by the company SEPPIC (CTFA name: sodium polyacryloyldimethyltaurate/polysorbate 80/sorbitan oleate); copolymers of 2-acrylamido-2-methylpropanesulfonic acid and of hydroxyethyl acrylate, for instance Simulgel NS and Sepinov EMT 10 sold by the company SEPPIC; cellulose derivatives such as hydroxyethyl cellulose or cetyl hydroxyethyl cellulose; polysaccharides and especially gums such as xanthan gum and hydroxypropyl guar gums; silicas, for instance Bentone Gel MIO sold by the company NL Industries or Veegum Ultra sold by the company Polyplastic.

The thickeners may also be cationic, for instance Polyquaternium-37 sold under the name Salcare SC95 (Polyquaternium-37 (and) Mineral Oil (and) PPG-1 Trideceth-6) or Salcare SC96 (Polyquaternium-37 (and) Propylene Glycol Dicaprylate/Dicaprate (and) PPG-1 Trideceth-6) or other crosslinked cationic polymers, for instance those of the CTFA name Ethyl Acrylate/Dimethylaminoethyl Methacrylate Cationic Copolymer In Emulsion.

Organic Powder

According to a particular form of the invention, the compositions according to the invention will also contain an organic powder.

In the present patent application, the term "organic powder" means any solid that is insoluble in the medium at room temperature (25° C.).

As organic powders that may be used in the composition of the invention, examples that may be mentioned include polyamide particles and in particular those sold under the Orgasol names by the company Atochem; nylon-6,6 fibers, in particular the polyamide fibers sold by Etablissements P Bonte under the name Polyamide 0.9 Dtex 0.3 mm (INCI name: Nylon-6,6 or Polyamide 6,6) with a mean diameter of 6 μm, a weight of about 0.9 dtex and a length ranging from 0.3 mm to 1.5 mm; polyethylene powders; microspheres based on acrylic copolymers, such as those made of ethylene glycol dimethacrylate/lauryl methacrylate copolymer, sold by the company Dow Corning under the name Polytrap; polymethyl methacrylate microspheres, sold under the name Microsphere M-100 by the company Matsumoto or under the name Covabead LH85 by the company Wackherr; hollow polymethyl methacrylate microspheres (particle size: 6.5-10.5 μm) sold under the name Ganzpearl GMP 0800 by Ganz Chemical; methyl methacrylate/ethylene glycol dimethacrylate copolymer microbeads (size: 6.5-10.5 μm) sold under the name Ganzpearl GMP 0820 by Ganz Chemical or Microsponge 5640 by the company Amcol Health & Beauty Solutions; ethylene-acrylate copolymer powders, such as those sold under the name Flobeads by the company Sumitomo Seika Chemicals; expanded powders such as hollow microspheres and especially microspheres formed from a terpolymer of vinylidene chloride, acrylonitrile and methacrylate and sold under the name Expancel by the company Kemanord Plast under the references 551 DE 12 (particle size of about 12 μm and mass per unit volume of 40 kg/m$^3$), 551 DE 20 (particle size of about 30 μm and mass per unit volume of 65 kg/m$^3$), 551 DE 50 (particle size of about 40 μm), or the microspheres sold under the name Micropearl F 80 ED by the company Matsumoto; powders of natural organic materials such as starch powders, especially of crosslinked or non-crosslinked corn, wheat or rice starch, such as the powders of starch crosslinked with octenylsuccinic anhydride, sold under the name Dry-Flo by the company National Starch; silicone resin microbeads such as those sold under the name Tospearl by the company Toshiba Silicone, especially Tospearl 240; amino acid powders such as the lauroyllysine powder sold under the name Amihope LL-11 by the company Ajinomoto; particles of wax microdispersion, which preferably have mean sizes of less than 1 μm and especially ranging from 0.02 μm to 1 μm, and which are formed essentially from a wax or a mixture of waxes, such as the products sold under the name Aquacer by the company Byk Cera, and especially: Aquacer 520 (mixture of synthetic and natural waxes), Aquacer 514 or 513 (polyethylene wax) or Aquacer 511 (polymer wax), or such as the products sold under the name Jonwax 120 by the company Johnson Polymer (mixture of polyethylene and paraffin waxes) and under the name Ceraflour 961 by the company Byk Cera (micronized modified polyethylene wax); and mixtures thereof.

Suspending Agents

In order to improve the homogeneity of the product, use may also be made of one or more suspending agents which are preferably chosen from hydrophobic modified montmorillonite clays, such as hydrophobic modified bentonites or hectorites. Examples that may be mentioned include the product Stearalkonium Bentonite (CTFA name) (reaction product of bentonite and the quaternary ammonium stearalkonium chloride) such as the commercial product sold under the name Tixogel MP 250 by the company Sud Chemie Rheologicals, United Catalysts Inc. or the product Disteardimonium Hectorite (CTFA name) (reaction product of hectorite and distearyldimonium chloride) sold under the name Bentone 38 or Bentone Gel by the company Elementis Specialities.

Other suspending agents may be used, in the present case in hydrophilic media (aqueous and/or ethanolic). They may be cellulose, xanthan, guar, starch, locust bean or agar derivatives.

The suspending agents are preferably present in amounts ranging from 0.1% to 5% by weight and more preferentially from 0.2% to 2% by weight relative to the total weight of the composition.

The amounts of these various constituents that may be present in the cosmetic composition according to the invention are those conventionally used in compositions for treating perspiration.

Aerosols

The compositions according to the invention may also be pressurized and may be conditioned in an aerosol device formed by:

(A) a container comprising an antiperspirant composition as defined previously, (B) at least one propellant and one means for dispensing said aerosol composition.

The propellants generally used in products of this type and that are well known to those skilled in the art are, for instance, dimethyl ether (DME); volatile hydrocarbons such as n-butane, propane, isobutane and mixtures thereof, optionally with at least one chlorohydrocarbon and/or fluorohydrocarbon; among these derivatives, mention may be made of the compounds sold by the company DuPont de Nemours under the names Freon® and Dymel®, and in particular monofluorotrichloromethane, difluorodichloromethane, tetrafluorodichloroethane and 1,1-difluoroethane sold especially under the trade name Dymel 152 A by the company DuPont. Use may also be made, as propellant, of carbon dioxide gas, nitrous oxide, nitrogen or compressed air.

The compositions containing perlite particles as defined previously and the propellant(s) may be in the same compartment or in different compartments in the aerosol container. According to the invention, the concentration of propellant generally varies from 5% to 95% by weight of pressurized composition, and more preferentially from 50% to 85% by weight relative to the total weight of the pressurized composition.

The dispensing means, which forms a part of the aerosol device, is generally constituted of a dispensing valve controlled by a dispensing head, which itself comprises a nozzle via which the aerosol composition is vaporized. The container containing the pressurized composition may be opaque or transparent. It may be made of glass, polymer or metal, optionally coated with a protective varnish coat.

The expressions "between . . . and . . . " and "ranging from . . . to . . . " or "at least . . . " should be understood as being limits inclusive, unless otherwise specified.

The examples and figures that follow are presented as nonlimiting illustrations of the invention. The compounds are, depending on the case, cited as the chemical names or as the CTFA (International Cosmetic Ingredient Dictionary and Handbook) names.

In these examples, the amounts of the composition ingredients are given as weight percentages relative to the total weight of the composition.

EXAMPLE 1—COMPOSITIONS A AND B ACCORDING TO THE INVENTION

Two compositions A and B according to the invention comprising spiculisporic acid were prepared according to a process that is standard for those skilled in the art, such as that given below;

dispersion of spiculisporic acid in water with stirring at room temperature gradual addition with stirring of the base to obtain the mole ratio R1 nmole base/nmoles S-acid=1.1

The mass of base to be used to neutralize the spiculisporic acid (S-acid) is defined in the following manner $$mass_{(base)}g = 2 \times \frac{mass_{(S-acid)}g}{MM_{(S-acid)}g \cdot mol^{-1}} \times MM_{(base)}g \cdot mol^{-1}$$

Empirical formulae and molecular masses of spiculisporic acid and of various bases that may be used according to the invention:

| | Empirical formula | Molar mass (g · mol$^{-1}$) |
|---|---|---|
| Spiculisporic acid | $C_{17}H_{28}O_6$ | 328.4 |
| Sodium hydroxide | NaOH | 40 |
| Potassium hydroxide | KOH | 56.1 |
| Triethanolamine (TEA) | $C_6H_{15}NO_3$ | 149.19 |
| L-Arginine | $C_6H_{14}N_4O_2$ | 174.2 |

Composition of the Formulations Prepared:

| Ingredients | Composition A: % of the ingredients | Composition B: % of the ingredients |
|---|---|---|
| Arginine (available under the name L-arginine ® sold by the company Ajinomoto) | Ratio $R_1$ = 1.1<br>5.84 | Ratio $R_1$ = 1.1<br>2.92 |
| Spiculisporic acid (available under the name Spiculisporic acid ® sold by the company Iwata Chemical) | 10 | 5 |
| Water | 84.16 | 92.08 |

EXAMPLE 2: DEMONSTRATION OF THE BACTERICIDAL ACTIVITY ON THE MICROORGANISM *CORYNEBACTERIUM XEROSIS* OF A COSMETIC COMPOSITION CONTAINING SPICULISPORIC ACID

Principle

Quantitative determination of the activity of a cosmetic formulation on *Corynebacterium xerosis*, a microorganism involved in phenomena associated with underarm odor. This microorganism is placed under optimum growth conditions.

Protocol

The model strain used is: *Corynebacterium xerosis*, Institut Pasteur Collection CIP 5216 (bacterium)

The strain is placed in contact with the test formulation in a suitable liquid culture medium in the following ratios:

10% of the microbial inoculum at $10^8$ microorganisms/ml

10% of the test formulation

80% of liquid culture medium (tryptocasein soya broth)

In parallel, a growth control, in which the test formulation is replaced with diluent (tryptone salt), is prepared under the same conditions.

The samples are placed in a rotary incubator at 35° C. and agitated throughout the duration of the test.

After 2, 6 and 24 hours of contact, the number of live microorganisms remaining in the mixture is evaluated.

The results are expressed as a logarithm of the number of microorganisms per milliliter of mixture.

Compositions

Compositions A and B according to the invention comprising spiculisporic acid, and control composition tested:

Composition A: aqueous 10% solution of spiculisporic acid neutralized with a base in a ratio Rbase/RS-acid=1.1

Composition B: aqueous 5% solution of spiculisporic acid neutralized with a base in a ratio Rbase/RS-acid=1.1

Results 24 hours after inoculation with 10% of a microbial inoculum containing $10^8$ microorganisms/ml, a decontamination of 6.6 Log and 4.9 Log relative to the growth control was obtained, respectively, with compositions A and B.

The change in the number of microorganisms per milliliter of sample (in Log) is presented in the tables below:

| *C. xerosis* (log) at | t0 | t2 h | t6 h | t24 h | difference *C. xerosis* (log) after 24 hours of contact time relative to the control |
|---|---|---|---|---|---|
| Composition A | 7.1 | <1.3 | <1.3 | 1.3 | <−6.6 |
| control | 7.1 | 7.1 | 7.0 | 7.9 | |

Relative to the growth controls, composition A has excellent activity on *C. xerosis* from 2 hours of contact (more than 5 Log of reduction).

| *C. xerosis* (log) at | t0 | t2 h | t6 h | t24 h | difference *C. xerosis* (log) after 24 hours of contact time relative to the control |
|---|---|---|---|---|---|
| Composition B | 7.1 | 4.4 | 3.5 | 3.0 | −4.9 |
| control | 7.1 | 7.1 | 7.0 | 7.9 | |

Relative to the growth controls, composition B has excellent antimicrobial activity on *C. xerosis* (reduction of 5 Log at 24 hours).

Spiculisporic acid in free form or in a form partially or totally neutralized with at least one mineral and/or organic base may thus be used in a composition that can thus inhibit the growth of *Corynebacterium xerosis*, of use for the treatment of unpleasant odors produced by the decomposition of sweat.

EXAMPLE 2: DEODORANT FORMULATION: ROLL-ON (Mass % Relative to the Total Mass of the Composition)

| | |
|---|---|
| Fragrance | 0.7 |
| Xanthan gum | 0.6 |
| Propanediol | 5 |
| 96% alcohol and water | 45 |
| Spiculisporic acid | 5 |
| Arginine | 2.92 |
| Glyceryl caprylate | 1.5 |
| Water | qs 100 |

The composition produces a deodorant effect.

EXAMPLE 3: DEODORANT FORMULATION: ROLL-ON (Mass % Relative to the Total Mass of the Composition)

| | |
|---|---|
| Fragrance | 1 |
| Xanthan gum | 0.4 |
| Pectin | 2 |
| Mixture of: | |
| Caprylic/capric acid triglycerides Jojoba oil, and Dioctyl ether | 20 |
| Spiculisporic acid | 5 |
| Arginine | 3 |
| Calcium carbonate | 0.05 |
| Preserving agent | 0.5 |
| Water | qs 100 |

The composition produces a deodorant effect.

The invention claimed is:

1. A cosmetic process for treating human body odors which comprises applying to human keratin materials, as a deodorant active agent, at least one of: a neutralized spiculisporic acid in a form that is partially neutralized with at least one mineral base, totally neutralized with at least one mineral base, partially neutralized with at least one organic base, totally neutralized with at least one organic base, or combinations thereof; or a composition containing the at least one neutralized spiculisporic acid in a physiologically acceptable medium.

2. The process as claimed in claim 1, in which the neutralized spiculisporic acid is contained in a composition comprising a physiologically acceptable medium.

3. The process as claimed in claim 2, in which the neutralized spiculisporic acid is present in the composition in a content of between 0.1% and 15% by weight relative to the total weight of the composition.

4. The process as claimed in claim 2, in which the neutralized spiculisporic acid is contained in a composition comprising at least one surfactant.

5. The process as claimed in claim 2, in which the neutralized spiculisporic acid is in a form that is partially neutralized with at least one organic base, or totally neutralized with at least one organic base.

6. The process as claimed in claim 2, in which the organic base is chosen from the group formed from basic amino acids, basic oligopeptides, basic amines, and mixtures thereof.

7. The process as claimed in claim 1, in which the neutralized spiculisporic acid is in a form that is partially neutralized with at least one organic base, or totally neutralized with at least one organic base.

8. The process as claimed in claim 7, in which the organic base is chosen from the group formed from basic amino acids, basic oligopeptides and basic amines, and mixtures thereof.

9. The process as claimed in claim 1, in which the organic base is chosen from the group formed from basic amino acids, basic oligopeptides and basic amines, and mixtures thereof.

10. The process as claimed in claim 1, in which the organic base is chosen from the group formed from arginine and triethanolamine, and mixtures thereof.

11. The process as claimed in claim 1, in which the ratio $R_1$ of the number of moles of the base to the number of moles of the neutralized spiculisporic acid is strictly greater than 1.0.

12. The process as claimed in claim 1, in which the ratio $R_1$ of the number of moles of the base to the number of moles of the neutralized spiculisporic acid is strictly greater than 1.0 and less than or equal to 2.50.

13. The process as claimed in claim 1, in which the ratio $R_1$ of the number of moles of the base to the number of moles of the neutralized spiculisporic acid is greater than or equal to 1.10 and less than or equal to 2.0.

14. A cosmetic process for treating human body odors which comprises applying to human keratin material selected from the group consisting of armpits or feet: at least one neutralized spiculisporic acid as claimed in claim 1; or a composition containing the at least one neutralized spiculisporic acid as claimed in claim 1 in a physiologically acceptable medium.

15. The process as claimed in claim 1, in which the neutralized spiculisporic acid is contained in a composition comprising a physiologically acceptable medium that also comprises an aqueous phase.

16. The process as claimed in claim 1, in which the organic base is arginine.

17. The cosmetic method as claimed in claim 1, wherein the at least one neutralized spiculisporic acid acts to treat human body odors by reducing the growth of *Corynebacterium xerosis*.

18. The process as claimed in claim 1, in which the at least one neutralized spiculisporic acid is contained in a composition comprising a physiologically acceptable medium, and is applied to human keratin material in the form of a roll-on or stick.

19. The process as claimed in claim 1, wherein the at least one neutralized spiculisporic acid is applied to armpits.

* * * * *